(12) United States Patent
Huang et al.

(10) Patent No.: US 10,258,058 B2
(45) Date of Patent: Apr. 16, 2019

(54) METHOD FOR PREPARING FUNCTIONAL EDIBLE OIL RICH IN PHYTOSTEROL ESTERS AND DIGLYCERIDES

(71) Applicant: OIL CROPS RESEARCH INSTITUTE, CHINESE ACADEMY OF AGRICULTURAL SECIENCES, Wuhan, Hubei (CN)

(72) Inventors: Fenghong Huang, Hubei (CN); Mingming Zheng, Hubei (CN); Shi Wang, Hubei (CN); Xia Xiang, Hubei (CN); Jie Shi, Hubei (CN); Qianchun Deng, Hubei (CN); Wenlin Li, Hubei (CN); Chuyun Wan, Hubei (CN)

(73) Assignee: OIL CROPS RESEARCH INSTITUTE, CHINESE ACADEMY OF AGRICULTURAL SECIENCES, Wuhan, Hubei (CN)

(*) Notice: Subject to any disclaimer, the term of this patent is extended or adjusted under 35 U.S.C. 154(b) by 0 days.

(21) Appl. No.: 15/588,667

(22) Filed: May 7, 2017

(65) Prior Publication Data

US 2017/0240935 A1 Aug. 24, 2017

Related U.S. Application Data

(63) Continuation-in-part of application No. 14/647,086, filed on May 23, 2015, now abandoned.

(51) Int. Cl.
*A23D 9/02* (2006.01)
*A23D 9/04* (2006.01)
(Continued)

(52) U.S. Cl.
CPC .............. *A23D 9/007* (2013.01); *A23D 9/013* (2013.01); *A23D 9/02* (2013.01); *A23D 9/04* (2013.01); *A61K 31/232* (2013.01); *A61K 31/575* (2013.01); *A61K 36/28* (2013.01); *A61K 36/31* (2013.01); *A61K 36/82* (2013.01); *C11B 3/12* (2013.01); *C11B 3/16* (2013.01);
(Continued)

(58) Field of Classification Search
None
See application file for complete search history.

(56) References Cited

U.S. PATENT DOCUMENTS 8,507,466 B2 * 8/2013 Plat .................. A23D 9/013
514/171
2003/0198727 A1 * 10/2003 Koike .................. A21D 2/16
426/601

* cited by examiner

*Primary Examiner* — Felicia C Turner

(57) ABSTRACT

A method for preparing functional edible oil rich in phytosterol esters and diglycerides includes steps of: 1) adding a raw material: adding phytosterol, triglyceride and a molecular sieve into a reactor, wherein a ratio of the phytosterol and the triglyceride is 1:2-1:4, a molecular sieve amount is 50 g/L; heating to 50-60° C. and stirring for 30-60 min, for obtaining a pre-mixture; 2) providing non-aqueous enzymatic transesterification: adding 5-20 g/L lipase into the pre-mixture, adding 100-200 ppm antioxidant, stirring and reacting for 8-12 h with a temperature of 50-60° C. and an atmospheric pressure, stopping heating and naturally cooling to a room temperature; and 3) post-treating: after reaction, removing the lipase and the molecular sieve by centrifugation, for obtaining the functional edible oil. The functional edible oil rich in two nutritional active components is obtained by the one-step method. Products of the present invention do not need separation and purification, and operation is simple.

5 Claims, 1 Drawing Sheet

(51) Int. Cl.
*C11B 3/12* (2006.01)
*C11B 3/16* (2006.01)
*C11C 3/00* (2006.01)
*C11C 3/04* (2006.01)
*C12P 7/64* (2006.01)
*A23D 9/007* (2006.01)
*A23D 9/013* (2006.01)
*A61K 36/28* (2006.01)
*A61K 36/31* (2006.01)
*A61K 36/82* (2006.01)
*C12P 33/00* (2006.01)
*A61K 31/232* (2006.01)
*A61K 31/575* (2006.01)

(52) U.S. Cl.
CPC ............. *C11C 3/003* (2013.01); *C11C 3/04* (2013.01); *C12P 7/6454* (2013.01); *C12P 33/00* (2013.01)

METHOD FOR PREPARING FUNCTIONAL EDIBLE OIL RICH IN PHYTOSTEROL ESTERS AND DIGLYCERIDES

CROSS REFERENCE OF RELATED APPLICATION

This is a Continuation-In-Parts application of the U.S. application Ser. No. 14/647,086, filed May. 23, 2015, which claims priority under 35 U.S.C. 119(a-d) to CN 201310335554.2, filed Aug. 4, 2013.

BACKGROUND OF THE PRESENT INVENTION

Field of Invention

The present invention relates to a method for preparing functional edible oil rich in phytosterol esters and diglycerides, and more particularly to a one-step method for preparing functional edible oil rich in phytosterol esters and diglycerides by enzymatic transesterification of phytosterol with triglyceride.

Description of Related Arts

Studies have shown that the phytosterol ester obtained by modifying phytosterol with esterification, is able to not only significantly improve fat-solubility thereof for expanding an application scope thereof in edible oil or greasy foods, but also reduce levels of serum cholesterol and serum triglycerides, which sufficiently reduces risk of cardiovascular disease. In addition, the absorption and utilization of phytosterol ester is five times of the ones of phytosterol, and phytosterol ester has a better lipophilicity and better cholesterol-lowering effect, which is a new functional food base. In 2010, phytosterol ester has been listed as a new food resource by the Ministry of Health of China. Diglyceride is structured lipid formed by bimolecular fatty acid respectively bonded to two terminal hydroxyl groups of glycerol. Compared with conventional triglyceride, diglyceride has fewer calories and is rarely converted into fat storing in the body. The diglyceride has functions such as lowering visceral fat, inhibiting weight gain, reducing blood neutral fat content, which is adaptable to prevention and treatment of hyperlipidemia and cardiovascular disease closely related to the hyperlipidemia. In 2000, US Food and Drug Administration listed the diglyceride as a generally recognized safe food after safety evaluation. Studies have shown that phytosterol ester cooperating with diglyceride is able to not only control weight, but also be used as functional foods, so as to prevent or reverse insulin and hyperlipidemia. However, natural phytosterol ester and diglyceride are rare, and generally need to be prepared by chemical methods.

Methods for preparing phytosterol ester and diglyceride are mainly chemical and enzymatic methods. The chemical method is simple, easy to control, and easy to be industrialized, which is the main method for preparing phytosterol ester. However, alkoxyl alkali metal compounds such as sodium methoxide and sodium ethoxide are used as the catalyst, which will cause corrosion of equipment. Meanwhile, a reaction temperature is high, consumption is high, byproducts are of great amount, and harmful solvents or water carriers usually used, which is not eco-friendly. The enzymatic method is mild and safe, which avoids side effects caused by high temperature, and the enzyme as a catalyst is re-useful, for reducing costs and eliminating toxic as well as residues. However, during preparation of preparing phytosterol ester and diglyceride with the conventional enzymatic method, problems, such as long reaction time, low conversion rate, and complex separation and purification of product, exist. Chinese patent 201110145589.0 discloses preparing functional edible oil, which contains phytosterol ester, by enzymatic method. However, a reaction temperature is up to 100° C., and the whole process must take place under nitrogen protection, which has a high requirement for reaction equipments and operating conditions is relatively high, and the phytosterol ester content in the functional edible oil obtained is low (<8%). Preparation of phytosterol ester and diglyceride usually requires different methods, respectively. Conventionally, one-step enzymatic method for preparing functional edible oil rich in two nutritional active components, phytosterol esters and diglycerides, has not been reported.

SUMMARY OF THE PRESENT INVENTION

An object of the present invention is to provide a method for preparing functional edible oil rich in phytosterol esters and diglycerides, wherein functional edible oil rich in two nutritional active components is able to be obtained by the one-step method. Products thereof do not need separation and purification, and operation thereof is simple.

Accordingly, in order to accomplish the above object, the present invention provides a method for preparing functional edible oil rich in phytosterol esters and diglycerides, comprising steps of:

1) adding a raw material: adding phytosterol (100-200 mM), triglyceride (200-1200 mM), reaction solvent (or no solvent) and a molecular sieve (50 g/L) into a reactor, wherein a ratio of the phytosterol and the triglyceride is 1:2-1:4, and a molecular sieve amount is 50 g/L (i.e. 50 g molecular sieve is added to each liter of the solvent; wherein a no-solvent method may be used, which means that the triglyceride is used as a solvent); heating to 50-60° C. and stirring, for obtaining a pre-mixture;

2) providing non-aqueous enzymatic transesterification: adding 5-20 g/L lipase (i.e. 5-20 g lipase is added to each liter of the pre-mixture) into the pre-mixture, adding 100-200 ppm antioxidant (i.e. an antioxidant concentration in the pre-mixture is 100-200 ppm), stirring and reacting for 8-12 h with a temperature of 50-60° C. (preferably 50° C.) and an atmospheric pressure, then stopping heating and naturally cooling to a room temperature; and 3) post-treating: after reaction, removing the lipase and the molecular sieve by centrifugation, and removing the reaction solvent by vacuum distillation (the reaction solvent is added to the reactor in the step 1), and is removed by vacuum distillation); for obtaining the functional edible oil rich in the phytosterol esters and the diglycerides.

In the method, the phytosterol is selected from a group consisting of sitosterol, brassicasterol and campesterol.

In the method, the triglyceride is selected from a group consisting of rapeseed oil, flaxseed oil, corn oil, tea seed oil, soybean oil, sunflower seed oil and microbial oil.

In the step 1) of the method, the raw material further comprises the reaction solvent, wherein the reaction solvent is dried by anhydrous sodium sulfate (during material pre-treatment), and a water content in the reaction solvent is controlled less than 0.1 wt %; a ratio of the phytosterol and the reaction solvent is 100-200 mmol:1 L; the reaction solvent is added to the reactor in the step 1), and is removed by vacuum distillation in the step 3); wherein the reaction solvent (which is for enzymatic esterification) is selected from a group consisting of isooctane, cyclohexane and n-heptane. The no-solvent solvent free method may be used, which means that the triglyceride is used as a solvent, and no other solvent is needed.

In the method, the lipase is in a free form or an immobilized form, which is *Candida rugosa* lipase, *Candida lipolytica* lipase, *Candida antarctica* lipase or *Pseudomonas cepacia* lipase obtained by microbial fermentation; preferably *Candida rugosa* lipase, *Candida antarctica* lipase and *Pseudomonas cepacia* lipase.

In the method, the antioxidant is a fat-soluble antioxidant which is natural vitamin E, fat-soluble tea polyphenols or L-ascorbyl palmitate; preferably fat-soluble tea polyphenols with an adding amount of 100-200 ppm.

The method further comprises a step of: pre-treating the raw material in the step 1): vacuum-drying the phytosterol at 80° C.-120° C. for 8-12 h, using refined vegetable oil as a source of the triglyceride; controlling a water content in the phytosterol less than 1 wt %, and controlling a water content in the triglyceride less than 0.2 wt %.

ADVANTAGES OF THE PRESENT INVENTION ARE AS FOLLOWS

1. The whole reaction is provided at a low temperature and the atmospheric pressure without nitrogen protection. Products thereof are stable and not easy to be oxidized. Equipments and operation thereof are simple.

2. The functional edible oil rich in two nutritional active components: phytosterol esters and the diglycerides, is able to be obtained by the one-step method. Products thereof almost do not need separation and purification, and reaction conditions thereof are mild.

3. By controlling the ratio of both raw materials (the phytosterol and the triglyceride) and the reaction conditions, functional edible oil with 10%-33% sterol phytosterol esters and 10%-30% diglycerides is able to be prepared, for suiting different product requirements.

DETAILED DESCRIPTION OF THE PREFERRED EMBODIMENT

Figure 1:
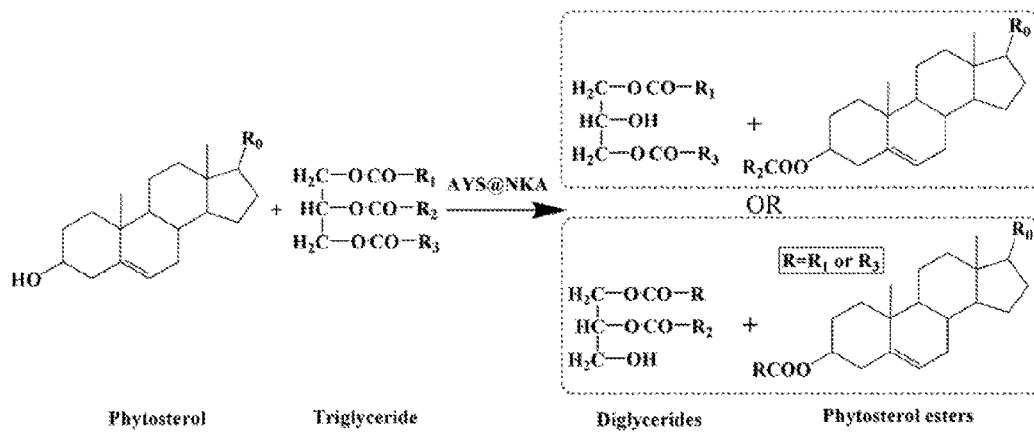
FIG. 1 is a schematic diagram of preparing functional edible oil rich in phytosterol esters and diglycerides of the present invention.

Preferred embodiments of the present invention as shown in the drawings and described are exemplary only and not intended to be limiting.

Preferred Embodiment 1

Figure 2:
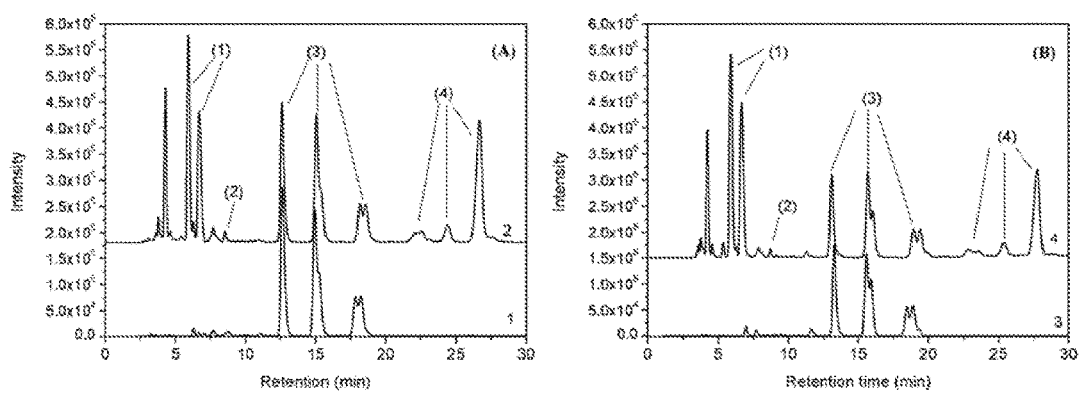
FIG. 2 is chromatograms of sunflower seed oil (A) and corn oil (B), and two corresponding functional edible oil of the present invention.

A method for preparing functional edible oil rich in phytosterol esters and diglycerides (a reaction formula thereof is shown in FIG. 1) comprises steps of:

(1) pre-treating a raw material: drying a reaction solvent (n-hexane) by anhydrous sodium sulfate (with a water content less than 0.1 wt %), vacuum-drying sitosterol (phytosterol) at 80° C. for 12 h (with a water content less than 1 wt %), and using refined sunflower seed oil (with a water content less than 0.2 wt %) as triglyceride;

(2) adding the raw material: adding 5 L isooctane, 207 g phytosterol (100 mM), 880 g sunflower seed oil (200 mM), and a molecular sieve (50 g/L) into a reactor, heating to 50° C. and stirring, for obtaining a pre-mixture;

(3) providing non-aqueous enzymatic transesterification: adding 25 g (5 g/L) *Candida antarctica* lipase into the pre-mixture, adding 200 ppm natural vitamin E antioxidant, stirring and reacting for 12 h with a temperature of 50° C. and an atmospheric pressure, then stopping heating and naturally cooling to a room temperature; and (4) post-treating: after reaction, removing the lipase (the *Candida antarctica* lipase) and the molecular sieve by centrifugation, and removing the n-hexane by vacuum distillation, wherein a total yield is more than 88%, a phytosterols esters content is about 31.6 wt %, a diglycerides content is about 27.7 wt %, a sunflower seed oil content is about 40.7 wt %, a product acid value is less than 1.0 mgKOH/g, and a peroxide value is less than 5.0 meq/kg, which illustrates that a product obtained according to the present invention is rich in two active functional components: phytosterols esters and diglycerides; wherein spectrograms of the sunflower seed oil and corresponding functional edible oil are shown in part A of FIG. 2.

Preferred Embodiment 2

A method for preparing functional edible oil rich in phytosterol esters and diglycerides comprises steps of:

(1) pre-treating a raw material: drying a reaction solvent (isooctane) by anhydrous sodium sulfate (with a water content less than 0.1 wt %), vacuum-drying stigmasterol (phytosterol) at 100° C. for 10 h (with a water content less than 1 wt %), and using refined rapeseed oil (with a water content less than 0.2 wt %) as triglyceride;

(2) adding the raw material: adding 5 L isooctane, 310.5 g phytosterol (150 mM stigmasterol), 2616 g rapeseed oil (600 mM), and a molecular sieve (50 g/L) into a reactor, heating to 55° C. and stirring;

(3) providing non-aqueous enzymatic transesterification: adding 50 g (10 g/L) *Candida antarctica* lipase, adding 150 ppm fat-soluble tea polyphenols antioxidant, stirring and reacting for 10 h with a temperature of 55° C. and an atmospheric pressure, then stopping heating and naturally cooling to a room temperature; and (4) post-treating: after reaction, removing the *Candida antarctica* lipase and the molecular sieve by centrifugation, and removing the isooctane by vacuum distillation, wherein a total yield is more than 85%, a phytosterols ester content is about 17.4 wt %, a diglyceride content is about 15.2 wt %, a rapeseed oil content is about 67.4 wt %, a product acid value is less than 1.0 mgKOH/g, and a peroxide value is less than 5.0 meq/kg, which illustrates that a product obtained according to the present invention is rich in two active functional components: phytosterols esters and diglycerides.

Preferred Embodiment 3

A method for preparing functional edible oil rich in phytosterol esters and diglycerides comprises steps of:

(1) pre-treating a raw material: drying a reaction solvent (n-heptane) by anhydrous sodium sulfate (with a water content less than 0.1 wt %), vacuum-drying brassicasterol at 120° C. for 8 h (with a water content less than 1 wt %), and using refined flaxseed oil (with a water content less than 0.2 wt %) as triglyceride;

(2) adding the raw material: adding 5 L n-heptane, 414 g phytosterol (200 mM brassicasterol), 5232 g rapeseed oil (1200 mM), and a molecular sieve (50 g/L) into a reactor, heating to 60° C. and stirring;

(3) providing non-aqueous enzymatic transesterification: adding 200 g (20 g/L) *Candida lipolytica* lipase, adding 100 ppm L-ascorbyl palmitate antioxidant, stirring and reacting for 12 h with a temperature of 60° C. and an atmospheric pressure, then stopping heating and naturally cooling to a room temperature; and (4) post-treating: after reaction, removing the lipase (the *Candida lipolytica* lipase) and the molecular sieve by centrifugation, and removing the n-heptane by vacuum distillation, wherein a total yield is more than 84%, the phytosterol esters content is about 12.0 wt %, the diglycerides content is about 10.5 wt %, the flaxseed oil content is about 77.5 wt %, a product acid value is less than 1.0 mgKOH/g, and a peroxide value is less than 5.0 meq/kg.

Preferred Embodiment 4

A method for preparing functional edible oil rich in phytosterol esters and diglycerides comprises steps of:

(1) pre-treating a raw material: vacuum-drying sitosterol (phytosterol) at 100° C. for 12 h (with a water content less than 1 wt %), and using refined tea seed oil (with a water content less than 0.2 wt %) as triglyceride, wherein no solvent is added, which means the tea seed oil is used as a reaction solvent;

(2) adding the raw material: adding 207 g phytosterol (100 mM), 2612 g tea seed oil (600 mM), and a molecular sieve (50 g/L) into a reactor, heating to 50° C. and stirring;

(3) providing non-aqueous enzymatic transesterification: adding 25 g (5 g/L) *Candida antarctica* lipase, adding 200 ppm natural vitamin E antioxidant, stirring and reacting for 12 h with a temperature of 50° C. and an atmospheric pressure, then stopping heating and naturally cooling to a room temperature; and (4) post-treating: after reaction, removing the lipase (the *Candida antarctica* lipase) and the molecular sieve by centrifugation, wherein a total yield is more than 83%, the phytosterol esters content is about 29.8 wt %, the diglycerides content is about 24.7 wt %, the tea seed oil content is about 45.5 wt %, the product acid value is less than 0.6 mgKOH/g, and the peroxide value is less than 5.0 meq/kg.

Preferred Embodiment 5

The preferred embodiment 5 is almost the same as the preferred embodiment 1, differences are: the *Candida antarctica* lipase is replaced by *Candida antarctica* immobilized lipase which is immobilized by ion exchange resin, wherein the immobilized lipase is prepared by dissolving the *Candida Antarctica* lipase in a disodium hydrogen phosphate solution and reacting with the ion exchange resin under stirring at 30° C. for 8 h. Functional edible oil rich in phytosterol esters and diglycerides is obtained, wherein a total yield is more than 92%, the sterol ester content is about 32.5 wt %, the diglyceride content is about 29.6 wt %, the sunflower seed oil content is about 37.9 wt %, the acid value is less than 0.8 mgKOH/g, and the peroxide value is less than 5.0 meq/kg.

Preferred Embodiment 6

The preferred embodiment 6 is almost the same as the preferred embodiment 1, differences are: in the step (1), the sunflower seed oil is replaced by soybean oil; the sitosterol is replaced by brassicasterol; and a reaction time is 8 h. Functional edible oil rich in phytosterol esters and diglycerides is obtained, wherein a total yield is more than 85%, the phytosterol esters content is about 20.2 wt %, the diglyceride content is about 18.9 wt %, the soybean oil content is about 60.9 wt %, the acid value is less than 0.8 mgKOH/g, and the peroxide value is less than 5.0 meq/kg.

Preferred Embodiment 7

The preferred embodiment 7 is almost the same as the preferred embodiment 1, differences are: in the step (1), the sunflower seed oil is replaced by corn oil; the sitosterol is replaced by a mixture of brassicasterol and sitosterol with a ratio of 1:1. Functional edible oil rich in phytosterol esters and diglycerides is obtained, wherein a total yield is more than 88%, the sterol ester content is about 30.2 wt %, the diglyceride content is about 28.4 wt %, the corn oil content is about 41.4 wt %, the acid value is less than 0.8 mgKOH/g, and the peroxide value is less than 5.0 meq/kg. Chromatograms of the corn oil and corresponding functional edible oil are shown in part B of FIG. 2.

Preferred Embodiment 8

The preferred embodiment 8 is almost the same as the preferred embodiment 1, differences are: in the step (1), the sunflower seed oil is replaced by microbial oil rich in DHA; the phytosterol is a mixture of stigmasterol and sitosterol with a ratio of 1:1. Functional edible oil rich in phytosterol esters and diglycerides is obtained, wherein a total yield is more than 84%, the sterol ester content is about 31.4 wt %, the diglyceride content is about 25.6 wt %, the microbial oil content is about 43.0 wt %, the acid value is less than 0.7 mgKOH/g, and the peroxide value is less than 4.0 meq/kg.

Preferred Embodiment 9

The preferred embodiment 9 is almost the same as the preferred embodiment 1, differences are: the *Candida antarctica* lipase is replaced by *Candida lipolytica* lipase, an amount of the natural vitamin E antioxidant is changed to 100 ppm. Functional edible oil rich in phytosterol esters and diglycerides is obtained, wherein a total yield is more than 85%, the sterol ester content is about 29.8 wt %, the diglyceride content is about 27.6 wt %, the sunflower seed oil content is about 42.6 wt %, the acid value is less than 0.8 mgKOH/g, and the peroxide value is less than 5.0 meq/kg.

Preferred Embodiment 10

The preferred embodiment 10 is almost the same as the preferred embodiment 1, differences are: the *Candida antarctica* lipase is replaced by *Pseudomonas cepacia* lipase, the flaxseed oil is replaced by a mixture of soybean oil and sunflower seed oil with a ratio of 1:1. Functional edible oil rich in phytosterol esters and diglycerides is obtained, wherein a total yield is more than 85%, the sterol ester content is about 28.6 wt %, a diglyceride content is about 27.4 wt %, the soybean oil content is about 20.2 wt %, the sunflower seed oil content is about 23.8 wt %, the acid value is less than 0.8 mgKOH/g, and the peroxide value is less than 5.0 meq/kg.

All raw materials according to the present invention, upper and lower limits as well as intervals according to the present invention, and upper and lower limits as well as intervals of technical parameters (such as temperature and time) are able to achieve the object, and no further embodiment will be provided.

What is claimed is:

1. A method for preparing functional edible oil rich in phytosterol esters and diglycerides, comprising steps of:

1) adding a raw material: adding phytosterols, triglyceride, a reaction solvent and a molecular sieve into a reactor, wherein a mole ratio of the phytosterols and the triglyceride is 1:2.5-1:4, a ratio of the phytosterol and the reaction solvent is 100-200 mmol:1 L, and a molecular sieve amount is 50 g/L; heating to 50-60° C. and thoroughly stirring, for obtaining a pre-mixture;

pre-treating the raw material: vacuum-drying the phytosterol at 80° C.–120° C. for 8-12 h, using refined vegetable oil as a source of the triglyceride; controlling a water content in the reaction solvent less than 0.1 wt %, controlling a water content in the phytosterol less than 1 wt %, and controlling a water content in the triglyceride less than 0.2 wt %;

2) providing non-aqueous enzymatic transesterification: adding 5-20 g/L lipase into the pre-mixture, adding 100-200 ppm antioxidant, stirring and reacting for 8-12 h with a temperature of 50-60° C. and an atmospheric pressure, then stopping heating and naturally cooling to a room temperature;

wherein the lipase is *Candida rugosa* lipase, *Candida lipolytica* lipase, *Candida antarctica* lipase or *Pseudomonas cepacia* lipase obtained by microbial fermentation;

3) post-treating: after reaction, removing the lipase and the molecular sieve by centrifugation, and removing the reaction solvent by vacuum distillation, for obtaining the functional edible oil with the phytosterol esters of 28.6 wt %-32.4 wt % and the diglycerides of 25.6 wt %-29.6 wt %, wherein a product acid value is less than 0.7 mgKOH/g, and a peroxide value is less than 4.0 meq/kg.

2. The method, as recited in claim 1, wherein the phytosterols is selected from a group consisting of sitosterol, brassicasterol and campesterol.

3. The method, as recited in claim 1, wherein the triglyceride is selected from a group consisting of rapeseed oil, flaxseed oil, soybean oil, sunflower seed oil, corn oil, tea seed oil and microbial oil.

4. The method, as recited in claim 1, wherein the reaction solvent is selected from a group consisting of isooctane, cyclohexane and n-heptane.

5. The method, as recited in claim 1, wherein the antioxidant is natural vitamin E, fat-soluble tea polyphenols or L-ascorbyl palmitate.

* * * * *